United States Patent
Ahmad et al.

(10) Patent No.: US 10,183,135 B2
(45) Date of Patent: Jan. 22, 2019

(54) ZERO PRESSURE START CONTINUOUS POSITIVE AIRWAY PRESSURE THERAPY

(71) Applicant: BREATHE TECHNOLOGIES, INC., Irvine, CA (US)

(72) Inventors: Samir S. Ahmad, San Diego, CA (US); Leonardo Alberto Baloa-Welzien, Lake Forest, CA (US)

(73) Assignee: Breathe Technologies, Inc., Irvine, CA (US)

(*) Notice: Subject to any disclaimer, the term of this patent is extended or adjusted under 35 U.S.C. 154(b) by 826 days.

(21) Appl. No.: 14/482,445

(22) Filed: Sep. 10, 2014

(65) Prior Publication Data

US 2015/0068529 A1    Mar. 12, 2015

Related U.S. Application Data

(60) Provisional application No. 61/876,127, filed on Sep. 10, 2013, provisional application No. 61/881,360, filed on Sep. 23, 2013.

(51) Int. Cl.
*A61M 16/00* (2006.01)
*A61M 16/06* (2006.01)
*A61M 16/10* (2006.01)

(52) U.S. Cl.
CPC .... *A61M 16/0069* (2014.02); *A61M 16/0003* (2014.02); *A61M 16/0051* (2013.01);
(Continued)

(58) Field of Classification Search
CPC .......... A61M 16/0051; A61M 16/0069; A61M 16/021; A61M 16/022; A61M 16/024;
(Continued)

(56) References Cited

U.S. PATENT DOCUMENTS 5,117,819 A * 6/1992 Servidio ............. A61M 16/024
                                                      128/204.18
5,134,995 A * 8/1992 Gruenke ............... A61M 16/00
                                                      128/204.21

(Continued)

OTHER PUBLICATIONS

Extended European Search Report for EP 14 844 856.6; dated Mar. 27, 2017.
(Continued)

*Primary Examiner* — Lynne Anderson
*Assistant Examiner* — Joseph D Boecker
(74) *Attorney, Agent, or Firm* — Stetina Brunda Garred & Brucker

(57) ABSTRACT

A respiratory assistance device is disclosed. There is a patient interface for coupling to a patient respiratory passageway, and a selectively regulated therapeutic gas flow source in pneumatic communication with the patient over the patient interface. A controller is connected to the therapeutic gas flow source and is receptive to inputs of a prescription pressure level and an initial delay duration. After the patient dons the patient interface, therapeutic gas flow is restricted for the initial delay duration following receipt of a treatment initiation command. Upon the expiry of the initial delay duration, the controller increases therapeutic gas flow to the prescription pressure level.

8 Claims, 3 Drawing Sheets

(52) U.S. Cl.
CPC .......... *A61M 16/024* (2017.08); *A61M 16/06* (2013.01); *A61M 16/107* (2014.02); *A61M 2016/0027* (2013.01); *A61M 2205/3344* (2013.01); *A61M 2205/42* (2013.01); *A61M 2205/52* (2013.01)

(58) Field of Classification Search
CPC ........ A61M 2205/50; A61M 2205/502; A61M 2205/52; A61M 16/00; A61M 16/0003; A61M 16/0057; A61M 16/0066; A61M 16/06; A61M 16/202; A61M 16/204; A61M 16/205
See application file for complete search history.

(56) References Cited

U.S. PATENT DOCUMENTS

| | | | |
|---|---|---|---|
| 5,199,424 A | 4/1993 | Sullivan et al. | |
| 5,492,113 A | 2/1996 | Estes et al. | |
| 5,503,146 A | 4/1996 | Froehlich et al. | |
| 5,704,345 A | 1/1998 | Berthon-Jones | |
| 6,029,665 A | 2/2000 | Berthon-Jones | |
| 6,138,675 A | 10/2000 | Berthon-Jones | |
| 6,363,933 B1 | 4/2002 | Berthon-Jones | |
| 6,401,713 B1* | 6/2002 | Hill | A61M 16/00 128/204.18 |
| 6,409,676 B2 | 6/2002 | Ruton et al. | |
| 6,467,477 B1* | 10/2002 | Frank | A61M 16/024 128/203.23 |
| 6,675,797 B1 | 1/2004 | Berthon-Jones | |
| 6,705,315 B2 | 3/2004 | Sullivan et al. | |
| 6,770,037 B2 | 8/2004 | Sullivan et al. | |
| 6,988,994 B2 | 1/2006 | Rapoport et al. | |
| 7,141,021 B2 | 11/2006 | Sullivan et al. | |
| 7,186,221 B2 | 3/2007 | Rapoport et al. | |
| 7,244,235 B2 | 7/2007 | Bowman et al. | |
| 7,320,320 B2 | 1/2008 | Berthon-Jones | |
| 7,757,690 B2 | 7/2010 | Stahmann et al. | |
| 7,882,834 B2 | 2/2011 | Gradon et al. | |
| 7,896,812 B2 | 3/2011 | Rapoport et al. | |
| 7,901,361 B2 | 3/2011 | Rapoport et al. | |
| 8,011,366 B2 | 9/2011 | Knepper | |
| 9,682,207 B2* | 6/2017 | Kwok | A61M 16/0051 |
| 2002/0023645 A1 | 2/2002 | Zdrojkowski et al. | |
| 2003/0111079 A1* | 6/2003 | Matthews | A61M 16/0051 128/204.18 |
| 2005/0133032 A1 | 6/2005 | Berthon-Jones | |
| 2005/0166920 A1 | 8/2005 | Delache et al. | |
| 2005/0211248 A1 | 9/2005 | Lauk et al. | |
| 2006/0102179 A1* | 5/2006 | Rapoport | A61B 5/0816 128/204.23 |
| 2009/0013999 A1* | 1/2009 | Bassin | A61M 16/00 128/204.18 |
| 2009/0038616 A1* | 2/2009 | Mulcahy | A61M 16/0051 128/204.23 |
| 2009/0205662 A1 | 8/2009 | Kwok et al. | |
| 2010/0095959 A1* | 4/2010 | Farrell | A61M 16/0051 128/202.13 |
| 2010/0108064 A1* | 5/2010 | Blackwell | A61M 16/0051 128/204.21 |
| 2010/0252041 A1 | 10/2010 | Kapust et al. | |
| 2011/0166470 A1 | 7/2011 | Rapoport et al. | |
| 2011/0253136 A1 | 10/2011 | Sweeney et al. | |
| 2012/0325211 A1 | 12/2012 | Allum et al. | |
| 2012/0325218 A1* | 12/2012 | Brambilla | A61M 16/0666 128/205.25 |
| 2013/0104883 A1 | 5/2013 | Lalonde | |
| 2014/0000610 A1* | 1/2014 | Rapoport | A61M 16/0666 128/204.23 |
| 2014/0123977 A1* | 5/2014 | Lalonde | A61M 16/0051 128/201.13 |

OTHER PUBLICATIONS

International Search Report and Written Opinion for PCT/US14/55025 (8 pages), dated Dec. 17, 2014.

\* cited by examiner

ZERO PRESSURE START CONTINUOUS POSITIVE AIRWAY PRESSURE THERAPY

CROSS-REFERENCE TO RELATED APPLICATIONS

This application relates to and claims the benefit of U.S. Provisional Application No. 61/876,127 filed Sep. 10, 2013 and entitled "ZERO PRESSURE START CONTINUOUS POSITIVE AIRWAY PRESSURE THERAPY" and U.S. Provisional Application No. 61/881,360 filed Sep. 23, 2013 and entitled "ZERO PRESSURE START CONTINUOUS POSITIVE AIRWAY PRESSURE THERAPY", the entire disclosures of which are hereby wholly incorporated by reference.

STATEMENT RE: FEDERALLY SPONSORED RESEARCH/DEVELOPMENT

Not Applicable

BACKGROUND OF THE INVENTION

1. Technical Field of the Invention

The present disclosure relates generally to the treatment of respiratory and cardiovascular conditions, and more particularly, to methods and systems for zero pressure start continuous positive airway pressure (CPAP) therapy.

2. Description of the Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles resulting from patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Earlier patient breathing assistance devices tended to be uncomfortable to use because of the bulkiness associated with the patient interface, as well as the misapplication of pressure resulting from sub-optimal control methodologies. Various improvements have been developed to reduce discomfort during therapy, particularly at critical points along the patient's respiratory cycle. Thus, what was previously prescribed only for the more severe cases of sleep apnea in which the benefits of treatment outweighed the significant discomfort is now useful for treating a wider spectrum of sleep apnea conditions.

Notwithstanding the increased availability of CPAP devices for home use as a result of these technical improvements, ensuring patient compliance with the prescribed treatment remains a challenge. One complaint is the discomfort associated with the application of pressure against the respiratory efforts of the patient during a waking state. The sense of asphyxiation associated with even a slight pressure and corresponding increase in work of breathing may be distracting enough to a patient such that merely falling asleep becomes difficult. Indeed, positive airway pressure may not be needed until the patient reaches a state of sleep since apnea conditions do not arise until such a state. Thereafter, the application of full therapeutic pressure as properly prescribed in accordance with the patient's condition generally does not interrupt the patient's sleep.

In order to minimize patient discomfort during the pre-sleep state, breathing assistance devices incorporate ramping, where delivered pressure is gradually increased over a set time period. There are a variety of delivery pressure increase curves, also referred to as ramp paths, which may be implemented by the device. These include linear ramp paths, a curved ramp path that increases delivery pressure at a higher rate in the initial time period of the ramp duration, a curved ramp path that increases delivery pressure at a higher rate in the later time period of the ramp duration, and so forth.

With or without ramping, treatment and airflow to the patient begin once the patient wears the interface in existing CPAP devices. Otherwise, exhaled carbon dioxide may accumulate inside the patient interface as well as the conduit between the patient interface and the CPAP device, leading to further discomfort and possible asphyxiation over the repeated inspiration of exhaled breathing gasses.

Again, activating the ventilation source while in the pre-sleep state, even at the low levels of pressure being delivered at the beginning of the ramping, may cause discomfort that prevents the patient from falling asleep. In existing CPAP systems, the patient simply must become accustomed to the slight discomfort at the beginning of treatment. Accordingly, there is a need in the art for a zero pressure start CPAP therapy.

BRIEF SUMMARY OF THE INVENTION

In accordance with various embodiments of the disclosure, a respiratory assistance device is contemplated. There may be a patient interface that can couple to a patient respiratory passageway. Additionally, there may be a selectively regulated therapeutic gas source in pneumatic communication with the patient over the patient interface. The patient interface includes a valve through which the patient can breathe spontaneously without additional pressure from the gas source. A controller may be connected to the therapeutic gas source and is receptive to inputs of a prescription pressure level and an initial delay duration. After the patient dons the patient interface, therapeutic gas from the source to the interface may be restricted for the initial delay duration following receipt of a treatment initiation command. Upon the expiry of the initial delay duration, the controller may increase therapeutic gas flow to the prescription pressure level.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION OF THE INVENTION

The detailed description set forth below in connection with the appended drawings is intended as a description of certain embodiments of the presently disclosed selective ramping of therapeutic pressure in a patient breathing apparatus, and is not intended to represent the only forms that may be developed or utilized. Generally, the apparatus delivers breathing gas to a patient for the treatment of obstructive sleep apnea (OSA) and other cardio-pulmonary conditions, and selectively augments and relieves pressure throughout the breathing cycle. The description sets forth the various functions in connection with the illustrated embodiments, but it is to be understood, however, that the same or equivalent functions may be accomplished by different embodiments that are also intended to be encompassed within the scope of the present disclosure. It is further understood that the use of relational terms such as first and second and the like are used solely to distinguish one entity from another without necessarily requiring or implying any actual such relationship or order between such entities.

Figure 1:
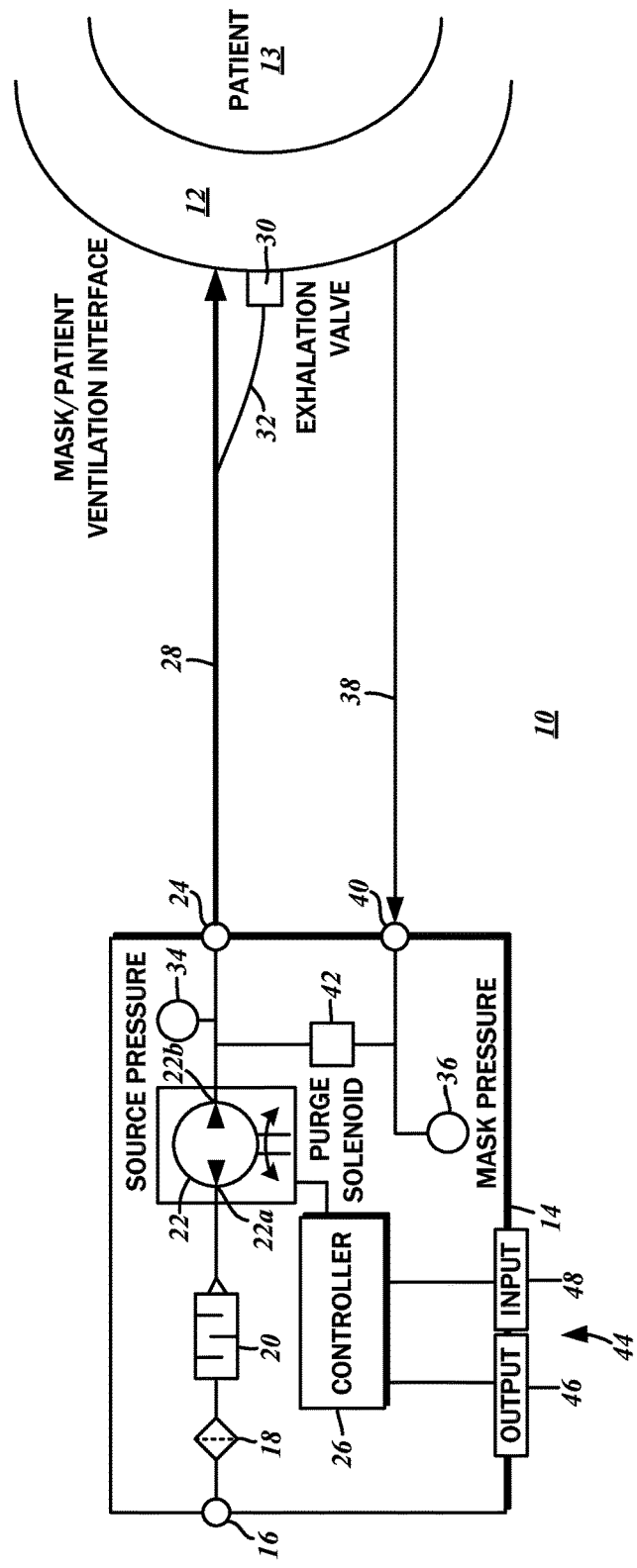
FIG. 1 is a block diagram showing the various components of a CPAP apparatus in accordance with various embodiments of the present disclosure including a typical ventilation unit, a patient ventilation mask, and gas passage conduits.

The block diagram of FIG. 1 illustrates an exemplary respiratory assistance device 10 in which various embodiments of the present disclosure may be implemented. There is a mask or patient ventilation interface 12, and a ventilation unit 14. The following disclosure will make reference to the patient ventilation interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for CPAP treatment in accordance with the present disclosure. The ventilation source 22 has an inlet port 22a coupled to the sound suppressor 20, and an outlet port 22b that is in gas flow communication with an outlet port 24 of the ventilation unit 14. The ventilation source 22 is driven electrically and its actuation is governed by a controller 26, which implements various methods of CPAP treatment such as those disclosed in the co-pending U.S. patent application Ser. No. 13/411,257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein.

The flow of breathing gas that is output from the ventilation source 22 is passed through the outlet port 24 to a gas conduit 28 that is in coupled to the aforementioned patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted valve 30 that is selectively actuated depending on the pressure differential between the patient ventilation interface 12 and the ventilation unit 14. The valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient ventilation interface 12, including the piloted valve 30 thereof, are presented by way of example only and not of limitation. Any other suitable patient ventilation interface 12, including those that may be utilized in conjunction with different variations of the ventilation unit 14, may be substituted without departing from the scope of the present disclosure.

In order to ascertain such pressure differentials, the presently contemplated respiratory assistance device 10 includes dual pressure sensors, including a source pressure sensor 34 and a patient interface sensor 36. The source pressure sensor 34 is disposed within the ventilation unit 14, and monitors the pressure at the outlet port 22b. The patient interface pressure sensor 36 is also physically disposed within the ventilation unit 14, but is in direct gas flow communication with the patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

As indicated above, the sequence and timing of delivering gas flow to the patient 13 are governed by the specific treatment modalities that utilize feedback data from the pressure sensors 34, 36. The setting of options relating to the treatment modalities, along with the starting and stopping of treatment is possible via a user interface 44 coupled to the controller 26, which includes an output or display interface 46, as well as an input interface 48.

Figure 2:
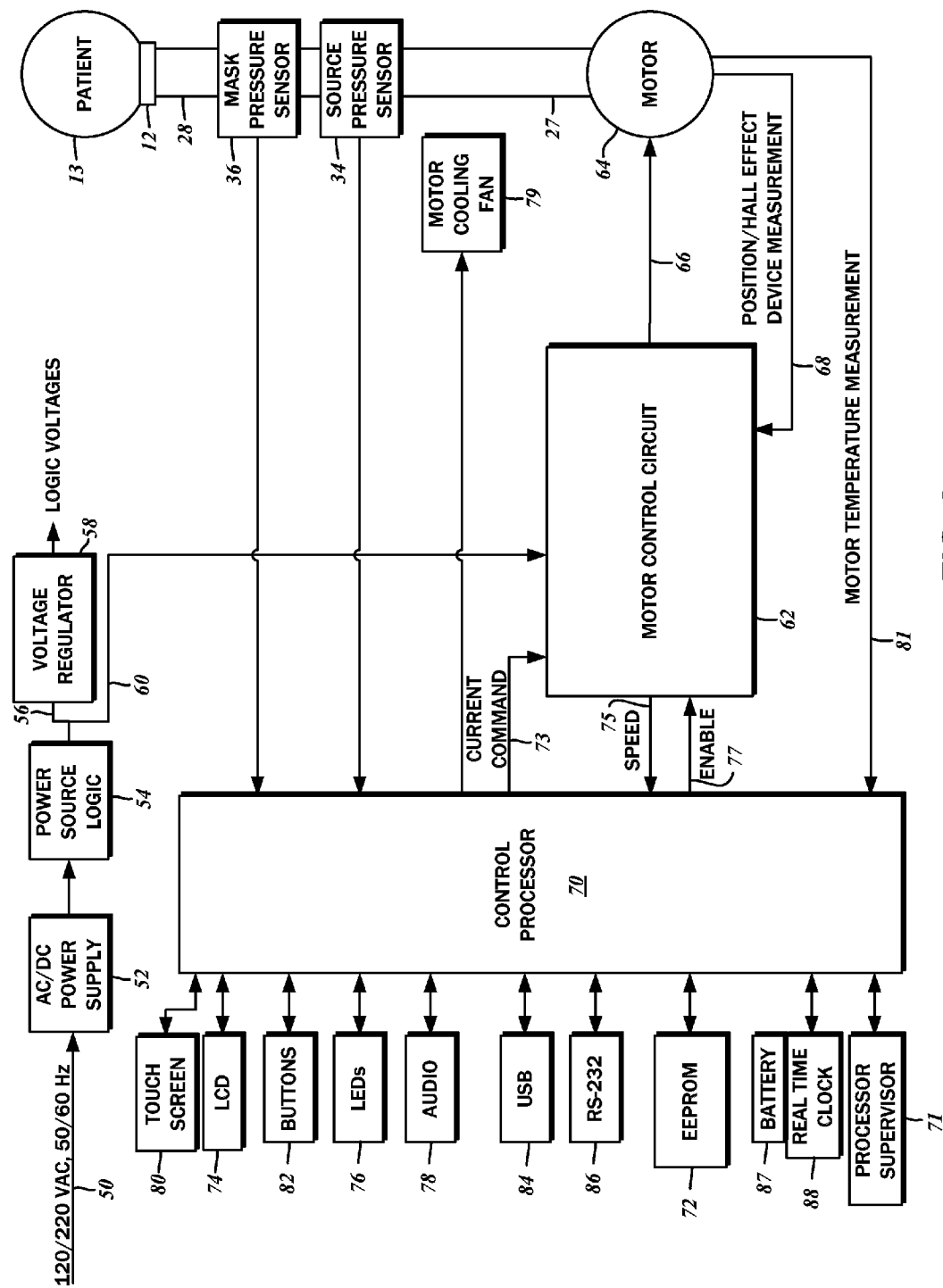
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 50. A power supply 52 is connected to the power source 50, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the ventilation source 22 utilizes a higher DC voltage than control logic devices, and thus the power supply 52 is connected to a power source logic 54. A first output 56 of the power source logic 54 is connected to an integrated circuit voltage regulator 58 that steps down the DC voltage to the logic device level of 5V. A second output 60 of the power source logic 54 is the existing high DC voltage directly from the power supply 52, and is connected to a motor control circuit 62.

The ventilation source 22 is comprised of several electrical components, including a motor 64 and the aforementioned motor control circuit 62. In accordance with one embodiment, the motor 64 is a brushless DC or electrically commutated motor. It will be recognized that the speed of rotation of the motor 64 is based upon input logic signals provided to the motor control circuit 62, which drives electrical current through its windings that induce magnetic fields that translate to rotational motion of the attached rotor. A fan coupled to the rotor thus rotates and generates a flow of air through an internal conduit 27. The internal conduit 27 is coupled to the outlet port 24, which is coupled to the gas conduit 28. As described above, the source pressure sensor 34 and the patient interface pressure sensor 36 are connected to the pneumatic circuit between the motor 64 and the patient 13.

The motor control circuit 62 has a motor drive output 66 that is connected to the motor 64. The rotational position of the motor 64 is detected by a Hall-effect sensor that is incorporated into the motor 64. An output voltage 68 from the Hall-effect sensor is fed back to the motor control circuit 62, which ensures that the actual position corresponds to the intended or commanded position.

The controller 26 and its functionality may be implemented with a programmable integrated circuit device such as a microcontroller or control processor 70. Broadly, the control processor 70 receives certain inputs, and based upon those inputs, generates certain outputs. The specific operations that are performed on the inputs may be programmed as instructions that are executed by the control processor 70. In this regard, the control processor 70 may include an arithmetic/logic unit (ALU), various registers, and input/output ports. Although external memory such as EEPROM (electrically erasable/programmable read only memory) 72 may be connected to the control processor 70 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 70 is powered by a low voltage DC supply from the voltage regulator 58.

As mentioned above, in order to set the operational parameters of the ventilation unit, and to initiate or terminate certain functions, a graphical user interface is provided. Such graphical user interface is generated on a display screen 74, which may be of a liquid crystal type (LCD). Any type of graphic may be shown on the display screen 74, though for more specific indicators, a simple light emitting diode (LED) device 76 may be utilized. It will be recognized that alarm conditions, power status, and the like may be indicated with the LED device 76. Audible outputs may also be produced with audio transducers 78 that are likewise connected to the control processor 70. Among the contemplated outputs that may be generated on the audio transducer 78 include simple beeps and alarms, as well as sophisticated voice prompts that provide information and instructions.

An operator may interact with the graphical user interface through different input devices such as a touch screen interface 80 that is overlaid on the display screen 72. It will be recognized that various graphic elements may be generated on the display screen 72, with touch inputs/interactions corresponding in position to those graphic elements being evaluated as a selection or activation of the same. Various touch screen interfaces, some of which may be directly integrated with the display screen 72, are known in the art. Besides touch screen inputs, buttons 82 may also be connected to the control processor 70 for similarly receiving user inputs. It is understood that the audio transducer 78 may also accept sound input in the form of voice commands, the processing of which is performed may be performed by the control processor 70.

Several modalities for connecting to and communicating with other data processing devices such as general-purpose computers are also contemplated. Accordingly, the control processor 70 may be connected to a universal serial bus (USB) controller 84. For more basic communications, there may be a serial RS-232 transceiver 86. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 70 is connected to a real time clock 88 that maintains a common clock cycle. Although a primary feature of the real time clock 88 is to maintain synchrony at a processor cycle level, longer term time data is also maintained. In order to retain such time data, the real time clock 88 may be powered independently of the primary power source 50, and there is accordingly a battery backup 87. Under heavy processing loads or unexpected program conditions, the control processor 70 may become unable to execute critical programmed steps in real-time. Thus, the control processor 70 may include a processor supervisor 71 that invokes a program execution break upon detecting such conditions. Typically, this is implemented as a step of clearing a memory variable periodically, and when that step is unable to take place because instruction execution is frozen or otherwise delayed, the processor supervisor 71 may cause a predetermined routine to be executed.

As mentioned above, the motor 64 is driven by the motor control circuit 62, which generates different outputs depending on signals received from the control processor 70. The signal to drive the motor 64 is generated on a current command line 73. For control processing on a broader level, feedback from the ventilation source 22 is utilized, and in the specific form of a speed or current measurement input 75 from the motor control circuit 62. Furthermore, as detailed below, pressure readings at the ventilation source 22 and the patient 13 are utilized to reach control decisions. Accordingly, the source pressure sensor 34 and the patient interface pressure sensor 36 are both connected to the control processor 70. The ventilation source 22 is activated and deactivated via a motor enable line 77. To ensure that the temperature of the motor 64 remains within operational parameters, a motor cooling fan 79 may be driven directly by the control processor 70. In some embodiments, there may be additional control circuitry that isolates the power source of the motor cooling fan 79 from the control processor 70. The decision to activate and deactivate the motor cooling fan 79 may be made in response to temperature readings from the motor 64, and so there is a motor temperature reading 81 passed to the control processor 70.

Notwithstanding the foregoing description of the particular respiratory assistance device 10, the contemplated method of operation and a system configured for such operation can be adapted to any other respiratory assistance device 10. Various embodiments of the present disclosure contemplate zero pressure start CPAP treatment. Generally, this refers to delivering no therapeutic gas to the patient 13 even though the patient 13 has already worn the interface 12. Actual treatment is delayed so as to minimize discomfort during the wakeful state, where any slight increase in airway pressure is immediately noticeable. Upon transitioning to a sleeping state, the airway can be splinted with full prescription pressure without disturbing the patient 13.

Figure 3:
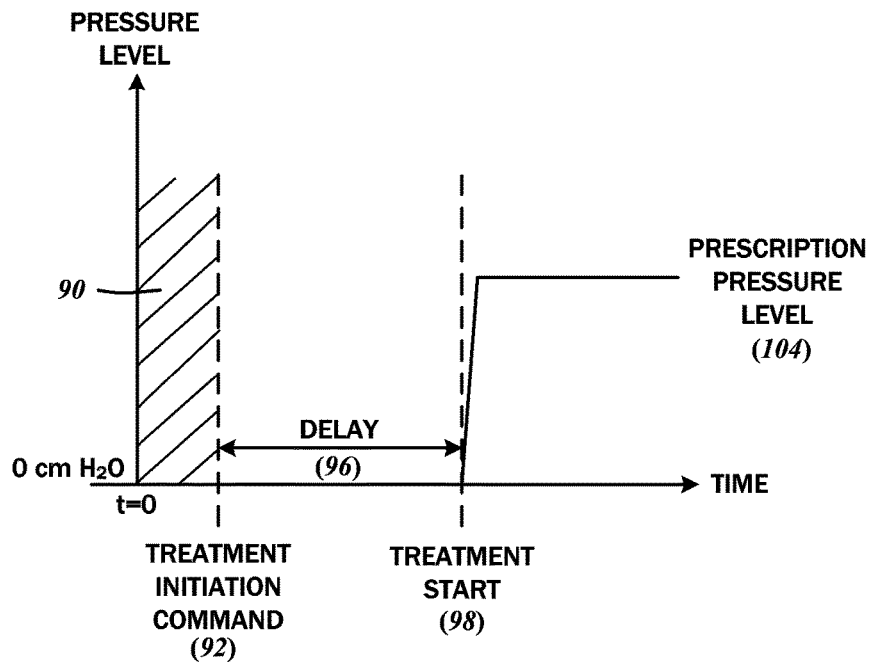
FIG. 3 a graph illustrating a zero pressure start therapeutic gas delivery to a patient in accordance with one embodiment of the present disclosure.

The graph of FIG. 3 broadly illustrates one embodiment of a zero pressure start, and the X-axis represents time, while the Y-axis represents the pressure level. After t=0, an indeterminate time period 90 prior to beginning CPAP treatment, the patient 13 dons the interface 12 while continuing to breathe. No therapeutic pressure is generated by the ventilation unit 14, and inspiratory and expiratory flow to the patient 13 occurs through the piloted valve 30. It is contemplated that the diameter of the gas conduit 28 is narrow and substantially restricts the flow of gas originating with the patient 13, whether that is inspiration or expiration.

In accordance with several implementations of the respiratory assistance device 10, the controller 26 accepts various inputs and generates responsive outputs to the ventilation source 22 to carry out the method of zero pressure start CPAP treatment of the present disclosure. As is the case with any real-time control system, the set points established by the controller 26 for the delivered therapeutic gas pressure 89 at any given instant in time may not necessarily correspond exactly to the true measurement thereof. The graph of FIG. 3 is an illustration of the ideal set points, and accordingly may not represent an actual measured response at the patient ventilation interface 12.

One of the accepted inputs is a treatment initiation command 92. For a predetermined delay 96, even though the ventilation unit 14 is activated, the controller does not actuate the ventilation source 22, and there continues to be little to no therapeutic pressure being delivered to the patient 13. Like the indeterminate time period 90 before the treatment initiation command 92 is provided, the patient 13 continues normal respiration through the valve 30. The duration of the delay 96 may be set by the user, and generally corresponds to the amount of time that the patient 13 takes to fall asleep under normal circumstances. According to one exemplary embodiment, this duration may be approximately five minutes, though other delay periods may be readily substituted without departing from the present disclosure. Following the delay 96, and presumably after the patient 13 has fallen asleep, the delivery of treatment pressure starts at time instant 98. In a basic implementation, the therapeutic gas delivered to the patient immediately increases within a short period of time to the prescription pressure level 104, that is, without any intentional delay introduced by the controller 26. It is understood that a truly instantaneous increase to prescription pressure is not possible due to the inherent physical system response delays. However, a more gradual ramp with further delays introduced by the controller 26 is also possible.

Figure 4:
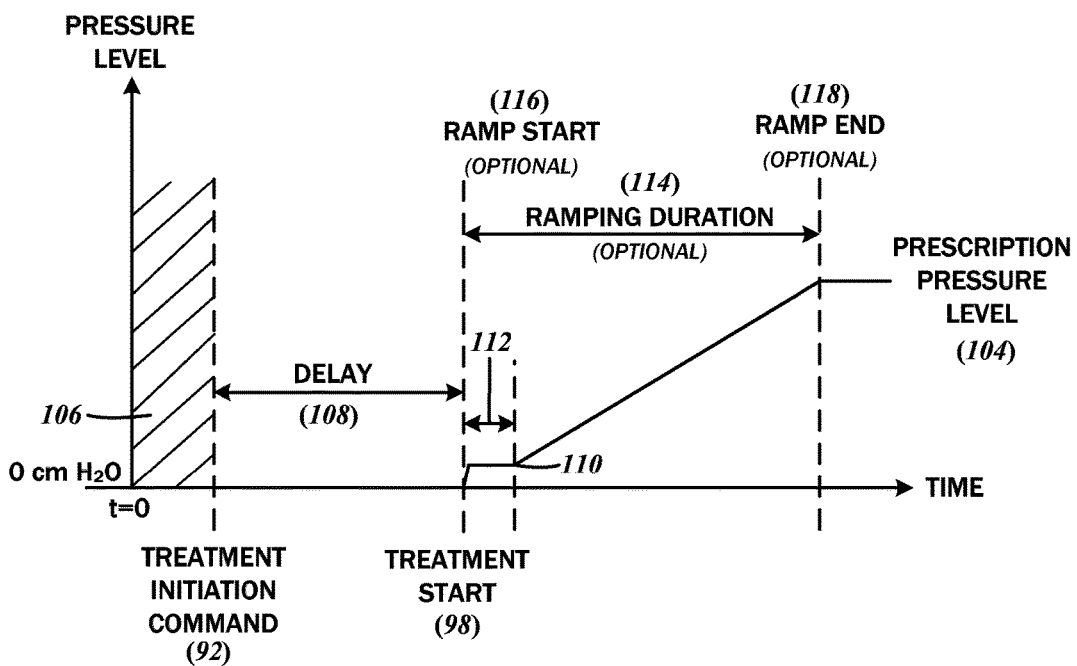
FIG. 4 is a graph illustrating another zero pressure start therapeutic gas delivery to a patient with an optional ramping function.

An alternative embodiment contemplates the use of a pressure ramp to gradually increase the delivered pressure from a lower value to the prescription level. With reference to the graph of FIG. 4, there is likewise an indeterminate period 106 after t=0 whereby the patient 13 dons the interface 12. Thereafter, the patient 13 provides the treatment initiation command 92, which initiates a zero pressure level delay 108 where little to no therapeutic pressure is delivered. Following the expiration of the delay 108, pressure delivery is begun at the treatment start 98, which also defines the beginning point of a total ramp duration 114. As noted, this embodiment utilizes a gradual ramping of therapeutic pressure that starts with a ramp base pressure level 110 that continues for a ramp delay 112, which is optional. It is also possible to begin the pressure increase upon expiry of the zero pressure level delay 108. At the end of the ramp delay 112, which is also defined as a ramp start point 116, the controller 26 is understood to increase the delivered therapeutic gas pressure 89 over the ramping duration 114, which concludes at a ramp end point 118. The delivered therapeutic gas pressure 89 is increased to the prescription pressure level 104, where it is maintained until the end of therapy or other exit condition.

The ramp delay 96 is contemplated to be user-adjustable, but is subject to the limitations imposed by the pre-defined total ramp duration 114. Additional details pertaining to adjustable ramping is disclosed in co-pending U.S. patent application Ser. No. 13/566,902 filed Aug. 3, 2012 and entitled Selective Ramping of Therapeutic Pressure in a Patient Breathing Apparatus, the entire disclosure of which is hereby wholly incorporated by reference.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:
1. A respiratory assistance device, comprising:
a patient interface for coupling to a respiratory passageway of a patient;
a selectively regulated therapeutic gas source in pneumatic communication with the patient over the patient interface; and
a controller connected to the therapeutic gas source and receptive to inputs of a prescription pressure level and an initial delay duration, delivery of therapeutic gas from the therapeutic gas source being restricted for the initial delay duration following receipt of a treatment initiation command, followed by an increase in therapeutic pressure to the prescription pressure level;
wherein the increase in the therapeutic pressure to the prescription pressure level is controlled over a predetermined ramp duration;

wherein the therapeutic pressure is increased to a ramp base pressure level by the controller after expiration of the initial delay duration, the increase in the therapeutic pressure to the prescription pressure level beginning at the ramp base pressure level;

wherein the therapeutic pressure is maintained at the ramp base pressure level by the controller after expiration of the initial delay duration for a ramp delay duration, the ramp delay duration being a predetermined amount of time adjustable by a user.

2. The respiratory assistance device of claim 1, wherein the patient interface includes a piloted exhalation valve that permits airflow to and from the respiratory passageway associated with spontaneous breathing while the delivery of therapeutic gas is being restricted.

3. The respiratory assistance device of claim 1, further comprising:
  a first pressure sensor in fluid communication with the patient interface; and
  a second pressure sensor in fluid communication with an output of the selectively regulated therapeutic gas source.

4. An article of manufacture comprising a program storage medium readable by a data processing apparatus, the medium tangibly embodying one or more programs of instructions executable by the data processing apparatus to perform a method for delivering therapeutic gas to a patient with a respiratory assistance device, the method comprising:
  receiving from the respiratory assistance device a prescription pressure level and a numeric value corresponding to a zero pressure delay duration;
  receiving from the respiratory assistance device a treatment initiation command following the patient being pneumatically coupled to the respiratory assistance device over a patient interface;
  restricting gas delivery from the respiratory assistance device to the patient interface at a zero pressure level for the zero pressure delay duration in response to receiving the treatment initiation command; and
  initiating gas delivery from the respiratory assistance device to the patient interface at the prescription pressure level after expiration of the zero pressure delay duration;
  wherein the gas delivery to the patient interface after expiration of the zero pressure delay duration is gradually increased to the prescription pressure level over a ramp duration based upon a ramp function;
  wherein gas delivery to the patient interface is increased to a ramp base pressure level after expiration of the zero pressure delay duration;
  wherein gas delivery to the patient interface is maintained at the ramp base pressure level after expiration of the zero pressure delay duration for a ramp delay duration, the ramp delay duration being a predetermined amount of time adjustable by a user.

5. The article of manufacture of claim 4, wherein the zero pressure delay duration corresponds to a predetermined time period for the patient to enter a sleep state.

6. The article of manufacture of claim 4, wherein the method further comprises:
  receiving from the respiratory assistance device a numeric value corresponding to the ramp duration.

7. The article of manufacture of claim 4, wherein the method further comprises:
  receiving from the respiratory assistance device a numeric value corresponding to the ramp delay duration.

8. A system comprising:
  the article of manufacture of claim 4; and
  the patient interface, wherein the patient interface includes a piloted exhalation valve through which the patient inhales and exhales spontaneously while gas delivery from the respiratory assistance device is restricted during the zero pressure delay duration.

* * * * *